US005679799A

United States Patent [19]
Isogai et al.

[11] Patent Number: 5,679,799
[45] Date of Patent: Oct. 21, 1997

[54] METHOD FOR PRODUCING OXYINDOLES

[75] Inventors: Katsuhisa Isogai; Kohei Hasegawa, both of Shizuoka-ken, Japan

[73] Assignee: K-I Chemical Industry Co., Ltd., Shizuoka-ken, Japan

[21] Appl. No.: 553,022

[22] Filed: Nov. 3, 1995

[30] Foreign Application Priority Data

Nov. 4, 1994 [JP] Japan ................................. 293654

[51] Int. Cl.$^6$ ................................. C07D 209/32
[52] U.S. Cl. ................................. 548/486
[58] Field of Search ................................. 548/486

[56] References Cited

FOREIGN PATENT DOCUMENTS 62-28133 6/1987 Japan.

OTHER PUBLICATIONS

R. Abramovitch et al, Internuclear Cyclisation. Part VIII.* Naphth[3 :2:1–cd]oxindoles., J. Chem. Soc.; 1954 p. 1697–1703.
T.V. RajanBabu et al, α–Nitroarylation of Ketones and Esters: An Exceptionally . . ., J. Org. Chem.,51, p17041712 (1986).
Alexander B. Neill, A New Synthesis of Oxindole, J. Amer. Chem. Soc., vol. 75 p. 1508 (1953).
P. H. Groggins et al,Unit Processes in Organic Synthesis, International Student Edition, McGraw Hill, p. 388–397 (1933).

*Primary Examiner*—Jacqueline Haley
*Attorney, Agent, or Firm*—Birch, Stewart, Kolasch & Birch, LLP

[57] ABSTRACT

There is disclosed a method for producing oxyindoles, which comprises reacting a 2-halogenophenylacetic acid or its salt with ammonia in the presence of a copper salt catalyst, and heating a mixture of the produced 2-aminophenylacetic acid or its salt and oxyindoles in the presence of an acid catalyst, to subject the 2-aminophenylacetic acid or its salt to a ring-closure reaction. According to this method, relatively readily available 2-halogenophenylacetic acids are used as a starting raw material to industrially produce highly pure oxyindoles in high yield in one pot without involving complicated steps. Further, since the amination is carried out at a temperature greatly lower than that of the conventional art, the lowering of the pH of the reaction liquid can be suppressed. Therefore, the restrictions on the specifications of the reaction apparatus, such as corrosion prevention and pressure resistance, can be mitigated.

11 Claims, No Drawings

METHOD FOR PRODUCING OXYINDOLES

FIELD OF THE INVENTION

The present invention relates to a method for producing oxyindoles useful as raw materials for the synthesis of agrochemical agents, pharmaceuticals, and the like.

BACKGROUND OF THE INVENTION

Many phenyl nucleus-substituted indole derivatives are known to have biochemical effects, and they are utilized for agrochemical agents, pharmaceuticals, and the like. As the methods for producing oxyindoles and chloro-substituted indoles that will serve as raw materials for their synthesis, various techniques are suggested.

For example, there is suggested a method wherein ω-chloroacetoanilide or its nucleus chloro-substituted product is synthesized from aniline or its chloro-substituted product and chloroacetyl chloride, and the obtained product is subjected to a ring-closure reaction by heating it to 220° to 230° C. in the presence of aluminum chloride (e.g., R. A. Abramovitch et al., J. Chem. Soc., 1954, 1697–1704, or JP-A ("JP-A" means unexamined published Japanese patent application) No. 184108/1994); or a method wherein 2-nitrophenylacetic acid or its ester is catalytically reduced, thereby causing the ring closure in a reducing manner (e.g., G. Hahn et al., Chem. Ber., 74, 500–519 (1941), or T. V. RajanBabu et al., J. Org. Chem., 51, 1704–1712 (1986)). However, since, in the former method, the ring closure is made at a high temperature of 220° C. or above in the presence of aluminum chloride, the reaction apparatus is limited greatly. In the latter method, it can be pointed out that the industrial use of 2-nitrophenylacetic acids as a raw material is not preferable.

Alternatively, a method is known wherein 2-chlorophenylacetic acid is subjected to ammonolysis and ring closure simultaneously in ammonia water in the presence of a copper-series catalyst, to produce oxyindole (Alexander B. Neill, J. Amer. Chem. Soc., 75, 1508, (1953)). This method is advantageous in that the 2-chlorophenylacetic acid as a raw material is relatively readily available, and in that oxyindole can be produced in one step. However, since the reaction temperature is 155° to 165° C., which is relatively high, such problems exist as that the material of the reaction apparatus is restricted, and the yield is as low as 34 to 43%.

As an improvement of the above method using ammonolysis, a method is suggested wherein a 2-halogenophenylacetic acid ester is used as a starting raw material, and an amination reaction and a ring-closure reaction are carried out in ammonia water in the presence of a copper salt (JP-B ("JP-B" means examined Japanese patent publication) No. 28133/1987). In this method, it is surmised that the 2-halogenophenylacetic acid ester, as a raw material, undergoes ammonolysis in the reaction system through the corresponding acid amide. According to an Example thereof, from methyl 2-chlorophenylacetate, as a raw material, oxyindole is produced in a yield of 78%, which is improved over the yield of the above method carried out by Alexander B. Neill. However, since the reaction temperature is as high as 190° C., and ammonia gas is confined before the heating until the pressure is brought to 10 kg/cm²G, the pressure at the time of the reaction is increased greatly, which is a problem. Therefore, if the method is carried out industrially, this method is also restricted considerably as to the material of the reaction vessel and the specifications of the reaction apparatus. Further, the method has such problems as that, since the ester is used as a raw material, the cost is disadvantageous, and that the separation of ammonia and alcohol produced concomitantly, in recovering the ammonia after the reaction, becomes complicated.

Generally, when a halide is aminated in ammonia water, the pH of the reaction liquid is lowered due to the ammonium halide that is produced concomitantly at the time of the reaction. To suppress that, a suggestion is known wherein the reaction temperature is lowered (e.g., P. H. Groggins, Unit Processes in Organic Synthesis, International Student Edition, pp. 388–397, McGraw Hill). In carrying out such a reaction industrially, as the material of the reaction vessel, stainless steel is generally used. If the reaction is carried out with the reaction temperature lowered, it is very significant in view of the prevention of corrosion of the reaction vessel due to suppression of lowering of the pH and the less restricted pressure-resistance specifications of the apparatus due to the lowering of the reaction pressure.

SUMMARY OF THE INVENTION

Therefore, an object of the present invention is to provide a method for industrially producing oxyindoles of high purity in high yields from relatively readily available raw materials without involving complicated steps and with few restrictions on the reaction apparatus.

Other and further objects, features, and advantages of the invention will appear more fully from the following description.

DETAILED DESCRIPTION OF THE INVENTION

Taking the above object into account, the inventors have keenly studied and have identified that, in substituting the 2-position of a 2-halogenophenylacetic acid or its salt by an amino group, if the amination reaction is carried out highly selectively with the reaction temperature lowered considerably more than that of the conventional art, in the reaction product, generally, there is, in addition to the corresponding oxyindoles, 2-aminophenylacetic acid or its salt, which is a precursor thereof, in a large amount. It has been found that, after the catalyst and the excess ammonia are eliminated from this reaction product, when the remaining 2-aminophenylacetic acid or its salt is subjected to a ring-closure reaction by heating in the presence of an acid catalyst, for conversion to oxyindoles, highly pure oxyindoles can be obtained in high yield. Based on this finding, the present invention has been attained.

That is, the present invention provides:

(1) a method for producing oxyindoles represented by formula (II):

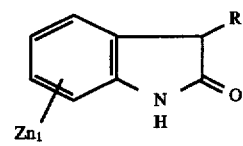

formula (II)

wherein Z represents a hydrogen atom, a halogen atom, an alkyl group, or an alkoxy group; R represents a hydrogen atom, an alkyl group, or an alkoxy group; and $n_1$ is an integer of 1 to 4; characterized in that the method comprises reacting a 2-halogenophenylacetic acid or its salt (hereinafter simply referred to as a 2-halogenophenylacetic acid in the description below) represented by formula (I):

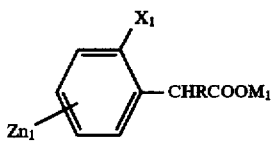

formula (I)

wherein $X_1$ represents a chlorine atom or a bromine atom; Z and R each have the same meanings as defined above; $M_1$ represents a hydrogen atom, an ammonium group, or an alkali metal; $X_1$ and Z are the same or different from each other; and $n_1$ has the same meaning as defined above, with ammonia in the presence of a copper salt catalyst, and heating a mixture of the produced 2-aminophenylacetic acid or its salt and oxyindoles represented by formula (II) in the presence of an acid catalyst, to cause ring-closure reaction of the 2-aminophenylacetic acid or its salt (hereinafter simply referred to as the 2-aminophenylacetic acid in the description below), and (2) the method for producing oxyindoles as recited in the above (1), wherein the amination is carried out by heating in ammonia water.

The phenyl group and/or methylene group of the 2-halogenophenylacetic acid that is used as a starting material in the method for producing oxyindoles in the present invention, may be replaced by a substituent that is not bulky and that does not inhibit the amination reaction and the ring-closure reaction thereafter. Preferably, Z is a hydrogen atom, a halogen atom (e.g., a fluorine atom, a chlorine atom, a bromine atom), an alkyl group, or an alkoxy group; R is a hydrogen atom, an alkyl group, or an alkoxy group. This compound, 2-halogenophenylacetic acid may be free acids or ammonium salts or salts of alkali metals, such as potassium and sodium, with preference given to free acids.

Further, the 2-halogenophenylacetic acid used in the present invention is, preferaly, a compound represented by the following formula (III), and it specifically includes 2-chlorophenylacetic acid, 2-bromophenylacetic acid, 2,3-dichlorophenylacetic acid, 2,4-dichlorophenylacetic acid, 2,5-dichlorophenylacetic acid, 2,6-dichlorophenylacetic acid, 2-chloro-4-fluorophenylacetic acid, 2-chloro-5-fluorophenylacetic acid, 2-chloro-6-fluorophenylacetic acid, 2-chloro-5-bromophenylacetic acid, and 2,4,5-trichlorophenylacetic acid, with particular preference given to 2-chlorophenylacetic acid, 2,4-dichlorophenylacetic acid, 2,5-dichlorophenylacetic acid, and 2-chloro-5-bromophenylacetic acid. Oxyindoles represented by formula (IV) can be obtained from the compound of formula (III).

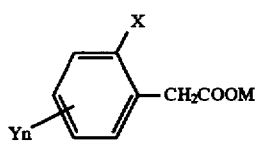

formula (III)

wherein X represents a chlorine atom or a bromine atom; Y represents a hydrogen atom, a fluorine atom, a chlorine atom, or a bromine atom; M represents a hydrogen atom, an ammonium group, or an alkali metal; X and Y are the same or different from each other; and n is an integer of 1 to 4.

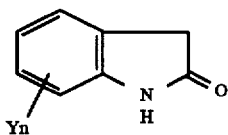

formula (IV)

wherein Y and n each have the same meanings as defined in formula (III).

For the amination reaction in the present invention, use is preferably made of a pressure-resistant reaction vessel, and the amination reaction is carried out in ammonia water, which also serves as a reaction solvent. The concentration of the ammonia water is preferably 10 to 50 wt %, more preferably 20 to 35 wt %. If the concentration of the ammonia is too low, 2-hydroxyphenylacetic acids, which are hydrolyzates, are increasingly produced concomitantly, and in addition the pH of the reaction system is lowered progressively, thereby adversely affecting the corrosion resistance of the reaction vessel. On the other hand, if the concentration of the ammonia is too high, the pressure at the time of the reaction becomes quite high. Therefore, in some cases, the specifications of the reaction apparatus are restricted or the recovery or the reuse of the ammonia water becomes disadvantageous.

Preferably the molar amount of ammonia to be used is 3 to 45 times, more preferably 6 to 35 times, the mol of the 2-halogenophenylacetic acid represented by formula (I). If the amount of ammonia to be used is too small, the stirring becomes difficult and the corrosion of the reaction apparatus is increased, in some cases. On the other hand, if the amount of ammonia is too large, the reaction result is not improved and the productivity is lowered.

The reaction temperature of the amination reaction of the present invention is 70° to 140° C., preferably 90° to 120° C., more preferably 100° to 110° C. If the reaction temperature is too low, the reaction rate is lowered. On the other hand, if the reaction temperature is too high, the amounts of colored or tarry incidental contaminants are increased, thereby lowering the yield and the quality of the product, and additionally the corrosion resistance and the pressure resistance of the reaction apparatus are restricted, in some cases.

The reaction pressure is dependent on the concentration of the ammonia water, the reaction temperature, and the like, and it is generally 5 to 8 kg/cm²G. Preferably the reaction time is generally 1 to 30 hours, more preferably 14 to 24 hours.

As the catalyst of the amination reaction of the method for producing oxyindoles of the present invention, a copper salt can be used, and a specific example is a univalent copper salt, such as cuprous chloride, cuprous bromide, cuprous iodide, and cuprous oxide, or a divalent copper salt, such as cupric chloride, cupric hydroxide, cupric oxide, and cupric sulfate, with preference given to a univalent copper salt, such as cuprous chloride, cuprous bromide, cuprous iodide, and cuprous oxide, in view of the reaction activity, the selectivity, etc.

The amount of the catalyst to be used is 0.001 to 1.0 gram-atom, preferably 0.05 to 0.3 gram-atoms, per mol of the 2-halogenophenylacetic acid represented by formula (I) in terms of the copper atom of the univalent copper salt or the divalent copper salt. If the amount of the catalyst is too small, the reaction rate is lowered and the unreacted raw material remains in a large amount. If the amount of the catalyst is too large, the procedure of removing the catalyst in the post-treatment becomes unpreferably complicated.

Thus the above reaction permits the conversion of the starting material to reach 93 to 100%.

The amination reaction of the present invention causes the conversion reaction to proceed satisfactorily, wherein the halogen atom in the 2-position of the phenyl group of the 2-halogenophenylacetic acid is replaced by an amino group. When the conversion has reached 90% or more, preferably 95% or more, the reaction of the first step is made to stop. At that time, although oxyindole is produced, it is not preferable to allow all the produced 2-aminophenylacetic acid to react long enough to form oxyindoles, because the 2-aminophenylacetic acid is thermally decomposed and colored contaminants are increased.

The product obtained in this way generally contains, in addition to the corresponding oxyindoles, 2-aminophenylacetic acid, which is a precursor thereof, in a large amount. Generally the composition is such that the oxyindoles amount to in the range of 20 to 70 mol %, preferably 30 to 60 mol %, in the total amount of the 2-aminophenylacetic acid and the oxyindoles in the product. After the copper salt catalyst and the excess ammonia are removed from the reaction product, an acid catalyst is added, and the 2-aminophenylacetic acid is subjected to a ring-closure by heating, thereby allowing highly pure oxyindoles to be obtained quickly in a high yield.

The removal of the copper salt catalyst and the excess ammonia can be carried out in a usual manner; for example, by distilling off the ammonia after treating with a suitable chelating resin and removing the resin of the copper complex. At that time, in order to decompose the ammonium salt produced by the amination reaction into free ammonia, and in order to suppress the thermal decomposition of the 2-aminophenylacetic acid, an alkali hydroxide is added, to make the reaction mixture alkaline, preferably to bring the pH to 10 or higher.

After the removal of the copper salt catalyst and the excess ammonia, a mineral acid, such as hydrochloric acid, hydrobromic acid, sulfuric acid, and phosphoric acid, or an organic acid, such as p-toluenesulfonic acid and methanesulfonic acid, is added, to make the reaction mixture acidic, preferably to adjust the pH to 2 to 5, more preferably to 2 to 3; and the intermingled 2-aminophenylacetic acid is subjected to a ring-closure by heating, to make oxyindoles. If the pH is lower than 2 and near 1, the 2-aminophenylacetic acid is easily decomposed, which is not preferable.

The heating temperature for the ring closure is preferably 30° to 100° C., more preferably 50° to 80° C. If the heating temperature is too high, the 2-aminophenylacetic acid is easily decomposed, which is not preferable. The heating time is several minutes to several hours, preferably 30 min to 3 hours.

By analyzing the reaction product, for example, by high-performance liquid chromatography, the conversion of the 2-aminophenylacetic acid to oxyindoles can be confirmed. At the time of heating for the ring closure, in the case of unsubstituted oxyindole that is high in solubility in water, the heating can be carried out with the reaction mixture in the state of an aqueous solution; while in the case of chloro-substituted oxyindoles or the like, which are low in solubility in water, the reaction mixture becomes an aqueous slurry, due to deposited crystals. Therefore in order to increase the ring-closure reaction rate, water or an inert solvent, such as a lower alcohol, for example, methanol and ethanol, or acetonitrile, may be added, as required.

After the ring-closure reaction, if necessary an aqueous alkali solution is added, to make the reaction product containing oxyindoles weakly alkaline, because the unreacted raw material and phenolic contaminants are converted into alkali metal salts, and they can be easily removed in the subsequent crystallization. Thereafter, oxyindoles are crystallized by cooling, and the crystals can be taken out by filtering, washing with water, drying, etc. Before the crystallization, if an activated-carbon treatment is carried out, or, if at the time of the crystallization, a suitable solvent, such as toluene and xylene, is added, the color of the product can be improved, sometimes.

It is preferable, in the production method of oxyindoles of the present invention, to carry out the course of processes from the amination to the completion of the ring-closure, without exposure to air or in an atmosphere of inert gas, such as nitrogen, helium, or argon.

According to the present invention, relatively readily available 2-halogenophenylacetic acids are used as a starting raw material to industrially produce highly pure oxyindoles in high yield in one pot without involving complicated steps.

Further, since, in the method for producing oxyindoles of the present invention, the amination is carried out at a temperature greatly lower than that of the conventional art, the lowering of the pH of the reaction liquid can be suppressed. Therefore, according to the present invention, the excellent effect is exhibited that the restrictions on the specifications of the reaction apparatus, such as corrosion prevention and pressure resistance, can be mitigated.

EXAMPLES

Now the present invention will be described based on the following Examples, but the present invention is not limited to them. The melting point in the Examples was measured using an FP-62-type automatic melting point measuring apparatus (manufactured by Mettler Instrumente AG.).

Example 1

(Synthesis of Oxyindole)

In a 3-liter stainless steel autoclave, were sealed 427 g (2.50 mol) of 2-chlorophenylacetic acid, 2040 g (30.0 mol) of 25% ammonia water, and, as a catalyst, 25.0 g (0.25 mol) of cuprous chloride. After the air in the autoclave was purged with nitrogen, they were allowed to react at 110° C. for 18 hours, with stirring. The internal pressure at the time of the reaction was 6.8 to 5.6 kg/cm$^2$G.

After the reaction, the amination reaction mixture was cooled to 30° C., and then it was taken out under sealing with nitrogen. The reaction mixture was analyzed by high-performance liquid chromatography, and it was identified that the conversion of the 2-chlorophenylacetic acid was 95.6%; oxyindole was produced in an amount of 33.4 mol %; 2-aminophenylacetic acid, which was the precursor thereof, was produced in an amount of 56.7 mol %; and the combined yield of the oxyindole and the 2-aminophenylacetic acid was 90.1%. In addition, 2-hydroxyphenylacetic acid was concomitantly produced, in an amount of 5.2%.

To the thus obtained reaction product, 416 g of a 48% aqueous sodium hydroxide solution was added. After the dissolved ammonia and catalyst were removed, about 330 g of 35% hydrochloric acid was added at 65° to 70° C., until the pH was brought to 2, and at that temperature the reaction mixture was stirred for 1 hour, to subject the remaining 2-aminophenylacetic acid to the ring-closure reaction, to form oxyindole.

Then, a 10% aqueous sodium hydroxide solution was added, to bring the pH to 8, and 2.5 g of powdered activated carbon was added, to carry out decoloration at 90° to 95° C., followed by heating and filtration. After adding 500 g of toluene, the mixture was cooled to room temperature, to cause crystallization. The deposited crystals were filtered, washed with water, and dried, to obtain 260 g (yield: 78.1%) of white crystals of oxyindole. Purity: 99.0% m.p.: 125.5° C.

Example 2

(Synthesis of 6-chlorooxyindole)

In a 3-liter stainless steel autoclave, were sealed 226 g (1.10 mol) of 2,4-dichlorophenylacetic acid, 2300 g (40.5 mol) of 30% ammonia water, and, as a catalyst, 21.8 g (0.22 mol) of cuprous chloride. After the air in the autoclave was purged with nitrogen, they were allowed to react at 100° C. for 22 hours, with stirring. The internal pressure at the time of the reaction was 8.2 to 7.5 kg/cm$^2$G.

After the reaction, the amination reaction mixture was cooled to 30° C., and then it was taken out. Then, 184 g of a 48% aqueous sodium hydroxide solution was added to the amination reaction mixture. After the dissolved ammonia and catalyst were removed, the reaction product was analyzed by high-performance liquid chromatography, and it was identified that the conversion of the 2,4-dichlorophenylacetic acid was 98.7%; the yield of 6-chlorooxyindole was 62.5%; and 2-amino-4-chlorophenylacetic acid was concomitantly produced, in an amount of about 20%.

After water was added to the reaction product, to bring the total amount to 4,000 g, about 140 g of 85% phosphoric acid was added at 75° to 80° C., to bring the pH to 3, so that crystals might be deposited. Further, the mixture was stirred at that temperature for 2 hours, to subject the remaining 2-amino-4-chlorophenylacetic acid to a ring-closure reaction, to form 6-chlorooxyindole.

Then, after a 10% aqueous sodium hydroxide solution was added to the thus obtained slurry, to bring the pH to 8, the mixture was cooled to room temperature, filtered, washed with water, and dried, to obtain 137 g (yield: 74.3%) of pale yellow crystals of 6-chlorooxyindole. m.p.: 192.4° C.

The crystals were dissolved in methanol in an amount of ten to fifteen times the amount of the crystals, by heating, followed by treatment with activated carbon, and then recrystallization was effected, to obtain white crystals of 6-chlorooxyindole. m.p.: 198.6° C.

$^1$H-NMR (DMSO-d$_6$+CDCl$_3$) δppm 3.43 (s, 1H, CH$_2$), 6.85 to 7.27 (m, 3H), 10.46 (s, br, D$_2$O replaceable 1H, CONH), IR (KBr, cm$^{-1}$) 3148, 3036, 1698, 1618, 1487, 1457, 1322, 1302, 933, 822, 561.

Example 3

The amination reaction of Example 1 was repeated, except that 50.0 g (0.50 mol) of cuprous chloride, which was twice the amount in Example 1, as a catalyst, was used.

After the reaction, the reaction mixture was analyzed by high-performance liquid chromatography, and it was identified that the conversion of the 2-chlorophenylacetic acid was 99.3%; oxyindole was produced in an amount of 37.8%; 2-aminophenylacetic acid, which was a precursor thereof, was produced in an amount of 54.0%; and the combined yield of the oxyindole and the 2-aminophenylacetic acid was 91.8%. In addition, 2-hydroxyphenylacetic acid was concomitantly produced, in an amount of 7.1%.

Then, similarly to Example 1, after a 48% aqueous sodium hydroxide solution was added to this reaction product, and the dissolved ammonia and catalyst were removed. Thereafter, the mixture was cooled to room temperature without carrying out the ring-closure treatment; the deposited crystals were filtered, washed with water, and dried, to obtain 114 g (yield: 34.2%) of pale brown oxyindole. Purity: 98.6%; and m.p.: 125.2° C.

Then, about 310 g of 50% sulfuric acid was added to the filtrate, to bring the pH to 2 to 3, and the mixture was heated and stirred at 60° C. for 1 hour, to subject the remaining 2-aminophenylacetic acid to a ring-closure reaction, to form oxyindole. Then, 10% sodium hydroxide was added thereto, to bring the pH to 8, followed by cooling to room temperature, to allow crystals to deposit. The deposited crystals were filtered, washed with water, and dried, to obtain 153 g (yield 45.9%) of pale brown oxyindole. Purity: 98.6% m.p.: 125.2° C.

The combined yield of oxyindole was 80.1%.

Comparative Example 1

Example 1 was repeated, except that the heat ring-closure treatment with 35% hydrochloric acid added was not carried out. The yield of oxyindole was 40%.

Comparative Example 2

Example 1 was repeated, except that, in place of 427 g (2.50 mol) of the 2-chlorophenylacetic acid, which was a raw material, 462 g (2.50 mol) of methyl 2-chlorophenylacetate was used.

After the amination reaction, although the conversion of the methyl 2-chlorophenylacetate was 100%, 2-chlorophenylacetamide was contained in an amount of 33 mol %. After the heat ring-closure operation with 35% hydrochloric acid added was carried out, the yield of oxyindole contained in the reaction liquid was 46.3%.

Comparative Example 3

Example 1 was repeated, except that, instead of 21.8 g (0.22 mol) of the cupric chloride, as a catalyst, 14.0 g (0.22 gram atom) of copper powder was used.

After the amination reaction, the recovery of the raw material was 99% or more, and the combined yield of oxyindole and 2-aminophenylacetic acid was less than 1%.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing oxyindoles represented by formula (II):

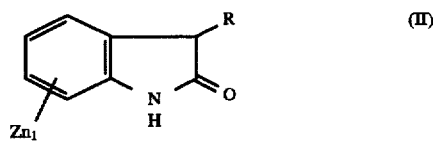

wherein Z represents a hydrogen atom, a halogen atom, an alkyl group, or an alkoxy group, R represents a hydrogen atom, an alkyl group, or an alkoxy group, and $n_1$ is an integer of 1 to 4, comprising step (1) of reacting a 2-halogenophenylacetic acid or its salt represented by formula (I):

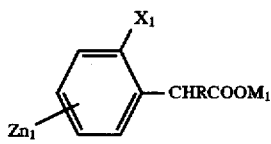

formula (I)

wherein $X_1$ represents a chlorine atom or a bromine atom; Z and R each have the same meanings as defined above; $M_1$ represents a hydrogen atom, an ammonium group, or an alkali metal; $X_1$ and Z are the same or different from each other; and $n_1$ has the same meaning as defined above, with ammonia in the presence of a copper salt catalyst to form a mixture of oxyindoles represented by formula (II) and 2-aminophenylacetic acid or its salt, and step (2) of, after removal of the copper salt catalyst and remaining ammonia from the mixture of oxyindoles represented by formula (II) and 2-aminophenylacetic acid or its salt, heating the mixture of oxyindoles represented by formula (II) and 2-aminophenylacetic acid or its salt in the presence of an acid catalyst, to cause ring-closure reaction of the 2-aminophenylacetic acid or its salt to form additional oxyindoles represented by formula (II) from said ring-closure reaction.

2. The method for producing oxyindoles as claimed in claim 1, wherein step (1) is carried out by heating in ammonia water.

3. The method for producing oxyindoles as claimed in claim 1, wherein the 2-halogenophenylacetic acid or its salt is a free acid, an ammonium salt, or an alkali-metal salt of one selected from the group consisting of 2-chlorophenylacetic acid, 2-bromophenylacetic acid, 2,3-dichlorophenylacetic acid, 2,4-dichlorophenylacetic acid, 2,5-dichlorophenylacetic acid, 2,6-dichlorophenylacetic acid, 2-chloro-4-fluorophenylacetic acid, 2-chloro-5-fluorophenylacetic acid, 2-chloro-6-fluorophenylacetic acid, 2-chloro-5-bromophenylacetic acid, and 2,4,5-trichlorophenylacetic acid.

4. The method for producing oxyindoles as claimed in claim 1, wherein the 2-halogenophenylacetic acid is a free acid.

5. The method for producing oxyindoles as claimed in claim 1, wherein the reaction temperature in step (1) is in the range of 70° to 140° C.

6. The method for producing oxyindoles as claimed in claim 1, wherein the copper salt catalyst is cuprous chloride, cuprous bromide, cuprous iodide, cuprous oxide, cupric chloride, cupric hydroxide, cupric oxide, or cupric sulfate.

7. The method for producing oxyindoles as claimed in claim 1, wherein an alkali hydroxide is added to the mixture after step (1) to make it alkaline prior to the removal of the copper salt catalyst and remaining ammonia from the mixture.

8. The method for producing oxyindoles as claimed in claim 1, wherein the reaction temperature at the ring-closure closure reaction in step (2) is in the range of 30° to 100° C.

9. The method for producing oxyindoles as claimed in claim 1, wherein the molar amount of ammonia to be used is 3 to 45 times the mol of the 2-halogenophenylacetic acid or its salt.

10. The method for producing oxyindoles as claimed in claim 1, wherein the amount of the copper salt catalyst to be used is 0.001 to 1.0 gram-atom per mol of the 2-halogenophenylacetic acid or its salt in terms of the copper atom of the copper salt.

11. The method for producing oxyindoles as claimed in claim 1, wherein steps (1) and (2) are carried out without exposure to air or in an atmosphere of inert gas.

* * * * *